US012256910B2

(12) United States Patent
Colter et al.

(10) Patent No.: US 12,256,910 B2
(45) Date of Patent: Mar. 25, 2025

(54) SYSTEM AND APPARATUS FOR ENHANCING THE ERGONOMICS OF A SURGICAL FOOT PEDAL

(71) Applicant: Johnson & Johnson Surgical Vision, Inc., Irvine, CA (US)

(72) Inventors: Jourdan Colter, Costa Mesa, CA (US); Brennen Wears, Mission Viejo, CA (US); Stephen Christopher, Philadelphia, PA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 588 days.

(21) Appl. No.: 17/330,189

(22) Filed: May 25, 2021

(65) Prior Publication Data

US 2021/0386412 A1    Dec. 16, 2021

Related U.S. Application Data

(60) Provisional application No. 63/037,948, filed on Jun. 11, 2020.

(51) Int. Cl.
*A61B 17/00*    (2006.01)

(52) U.S. Cl.
CPC .... *A61B 17/00* (2013.01); *A61B 2017/00973* (2013.01)

(58) Field of Classification Search
None
See application file for complete search history.

(56) References Cited

U.S. PATENT DOCUMENTS

| | | |
|---|---|---|
| D192,917 S | 5/1962 | Aymar et al. |
| D194,678 S | 2/1963 | Harry et al. |
| D234,085 S | 1/1975 | Stralhammer |
| 4,983,901 A | 1/1991 | Lehmer |
| 5,268,624 A | 12/1993 | Zanger |
| 5,342,293 A | 8/1994 | Zanger |
| 5,554,894 A | 9/1996 | Sepielli |
| 6,260,434 B1 | 7/2001 | Holtorf |
| 6,360,630 B2 | 3/2002 | Holtorf |
| 6,452,120 B1 | 9/2002 | Chen |
| 6,452,123 B1 | 9/2002 | Chen |
| 6,674,030 B2 | 1/2004 | Chen et al. |
| 6,962,581 B2 * | 11/2005 | Thoe ............. A61B 17/00 606/1 |
| D708,593 S | 7/2014 | Lynn et al. |
| 9,659,553 B1 | 5/2017 | Lawrence |
| D867,307 S | 11/2019 | Braaten et al. |
| D878,308 S | 3/2020 | Engler et al. |
| 10,747,255 B2 | 8/2020 | Gahler et al. |
| 10,901,450 B2 | 1/2021 | Jawidzik |
| 10,925,680 B2 | 2/2021 | Jawidzik |
| D911,982 S | 3/2021 | Colter et al. |

(Continued)

FOREIGN PATENT DOCUMENTS

WO    2019232002 A1    12/2019

*Primary Examiner* — Vicky A Johnson

(57) ABSTRACT

The present invention comprises a heel insert for use with a phacoemulsification foot pedal that may shift a surgeon's foot forward on the treadle of a foot pedal to reduce the force required to actuate the foot pedal. The present invention may be easily attachable and removable and may provide a less complicated and alternative foot position for surgeons preferring different treadle mechanics.

18 Claims, 5 Drawing Sheets

(56) References Cited

U.S. PATENT DOCUMENTS

| | | |
|---|---|---|
| D954,004 S | 6/2022 | Colter et al. |
| 2004/0035242 A1* | 2/2004 | Peterson .................. H01H 9/18 |
| | | 74/560 |
| 2004/0106915 A1 | 6/2004 | Thoe |
| 2005/0103607 A1 | 5/2005 | Mezhinsky |
| 2008/0067046 A1 | 3/2008 | Dacquay et al. |
| 2011/0106068 A1 | 5/2011 | Horvath et al. |
| 2013/0169412 A1 | 7/2013 | Roth |
| 2014/0135785 A1 | 5/2014 | Tran et al. |
| 2014/0364864 A1 | 12/2014 | Lynn et al. |
| 2015/0148615 A1 | 5/2015 | Brennan et al. |
| 2015/0173725 A1 | 6/2015 | Maxson et al. |
| 2017/0136159 A1* | 5/2017 | Mallough .............. A61M 1/804 |
| 2018/0132958 A1* | 5/2018 | Jochinsen .............. A61B 34/74 |

* cited by examiner

SYSTEM AND APPARATUS FOR ENHANCING THE ERGONOMICS OF A SURGICAL FOOT PEDAL

CROSS-REFERENCE TO RELATED APPLICATIONS

This application claims the benefit under 35 U.S.C. § 119(e) of U.S. Provisional Patent Application No. 63/037,948 filed Jun. 11, 2020, which is incorporated herein by reference in its entirety.

BACKGROUND

Field of Technology

The present disclosure relates generally to phacoemulsification surgical systems. In particular, the present disclosure relates to enhancing the ergonomics of a surgical foot pedal within phacoemulsification systems.

Description of the Background

Ophthalmic surgical apparatuses, such as phacoemulsification apparatuses, typically include operating controls for regulating parameters or functions of the apparatuses. A phacoemulsification apparatus is particularly directed to the surgical removal of the natural, crystalline lenses from cataractic eyes, such as to allow for and/or prior to the insertion of an artificial intraocular lens.

Such an apparatus typically includes a console, power supply, one or more pumps as well as associated electronic hardware for operating a multifunction surgical implement to ultrasonically emulsify eye tissue, irrigate the eye with a saline solution and aspirate the emulsified lens from the eye. Typically, such surgical implements are handheld.

In view of the handheld nature of the instrumentation necessary for a phacoemulsification procedure, it is generally desirable that the hands of a surgeon remain as free as possible during performance of a surgery. Accordingly, foot controls, such as in the form of a mechanical foot pedal, are frequently provided in order to facilitate use of the handpiece by delegating other control functions to the foot pedal device.

Any number of foot pedal device systems have been utilized which included a variety of pneumatic and electrical actuators to control the ophthalmic surgical apparatus. Improved foot pedal control systems, such as that described in U.S. Pat. No. 4,983,901 provide for a virtually unlimited number of control variations and modes for operating phacoemulsification apparatuses. Additional single linear and dual linear foot pedal patents include U.S. Pat. Nos. 5,268,624; 5,342,293; 6,260,434; 6,360,630; 6,452,120; 6,452,123; and 6,674,030.

The foot pedal must be user friendly in order to provide a surgeon comfort and reliability in its use, so as not to initiate disruption of the surgeon's concentration when performing surgery. For example, during control of the foot pedal the surgeon's posture is influenced by efforts to prevent losing contact with the foot pedal, which is typically achieved by keeping one foot flexed above the pedal and loading the body weight on the other foot. This causes a non-ergonomic posture which can lead to physical discomfort, and sometimes mistakes in control of the foot pedal.

Despite the availability of a number of relatively effective foot pedal designs, there is a need for a more ergonomically flexible foot pedal that enhances surgeon comfort and concentration. More specifically, there exists a need for an insertable heel extension that can be place into existing foot pedals.

SUMMARY

The present invention comprises a heel insert for use with a phacoemulsification foot pedal that may shift a surgeon's foot forward on the treadle of a foot pedal to reduce the force required to actuate the foot pedal. The present invention may be easily attachable and removable and may provide a less complicated and alternative foot position for surgeons preferring different treadle mechanics. Similarly, the present invention may shift the heel of the surgeon forward on the treadle of the foot pedal, thus shifting the pivot angle which may reduce heel rise during foot pedal activation.

Various embodiments recite a surgical system, comprising a console comprising a plurality of modes for at least one physically associated surgical instrument, a foot pedal communicatively associated with said console and suitable for varying ones of the plurality of modes, and a heel cup insert configured to fit near the distal end of the foot pedal suitable for receiving the heel of a user, wherein the heel cup insert is attached to the foot pedal by a magnetic force. The heel cup insert may comprise a first top portion between the foot pedal and the heel of the user and a second top portion on which the heel of the user rests. The heel cup insert may also comprise at least one vertical wall portion for receiving the heel of the user. The heel cup insert may also comprise plurality of magnets that may be located towards the distal and/or proximate end of the heel cup insert to provide a magnetic force. The heel cup insert may also be used as a handle to carry the foot pedal.

Various embodiments recite a surgical system for phacoemulsification, comprising a foot pedal communicatively associated with a surgical console, a treadle portion on the foot pedal for receiving a user's heel, and a heel cup insert removably attached to the treadle portion. The heel cup insert may be located on the distal end of the treadle portion and may be attached to the treadle portion by a magnetic force. The heel cup insert may comprise a first top portion between the foot pedal and the heel of the user and a second top portion on which the heel of the user rests. The heel cup insert may comprise at least one vertical wall portion for receiving the heel of the user and may be attached to the treadle portion by a plurality of magnets.

DESCRIPTION OF THE DRAWINGS

The accompanying drawings are included to provide a further understanding of the invention and are incorporated in and constitute a part of this specification. The drawings illustrate disclosed embodiments and/or aspects and, together with the description, serve to explain the principles of the invention, the scope of which is determined by the claims.

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

DETAILED DESCRIPTION

It is to be understood that the figures and descriptions of the present disclosure have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

Foot pedal controls used with surgical consoles have, among many other parts, a foot treadle portion on which an operator may place their foot such that the treadle, may, for example, rotate about a hinge between the bottom of the treadle and the top of the treadle. Thus, with the heel of the user's foot resting at the bottom of the treadle, the upper portion of the user's foot may depress the treadle downwards thereby lowering the upper portion of the user's foot toward the base of the foot pedal and/or raising the heel portion of the treadle. This movement may result in the user's heel moving so as to not be seated comfortably against the base of the treadle which often includes a heel cup portion. The heel cup portion may be rounded to comfortably accept the heel of a user and may provide stability of use of the treadle.

Figure 1:
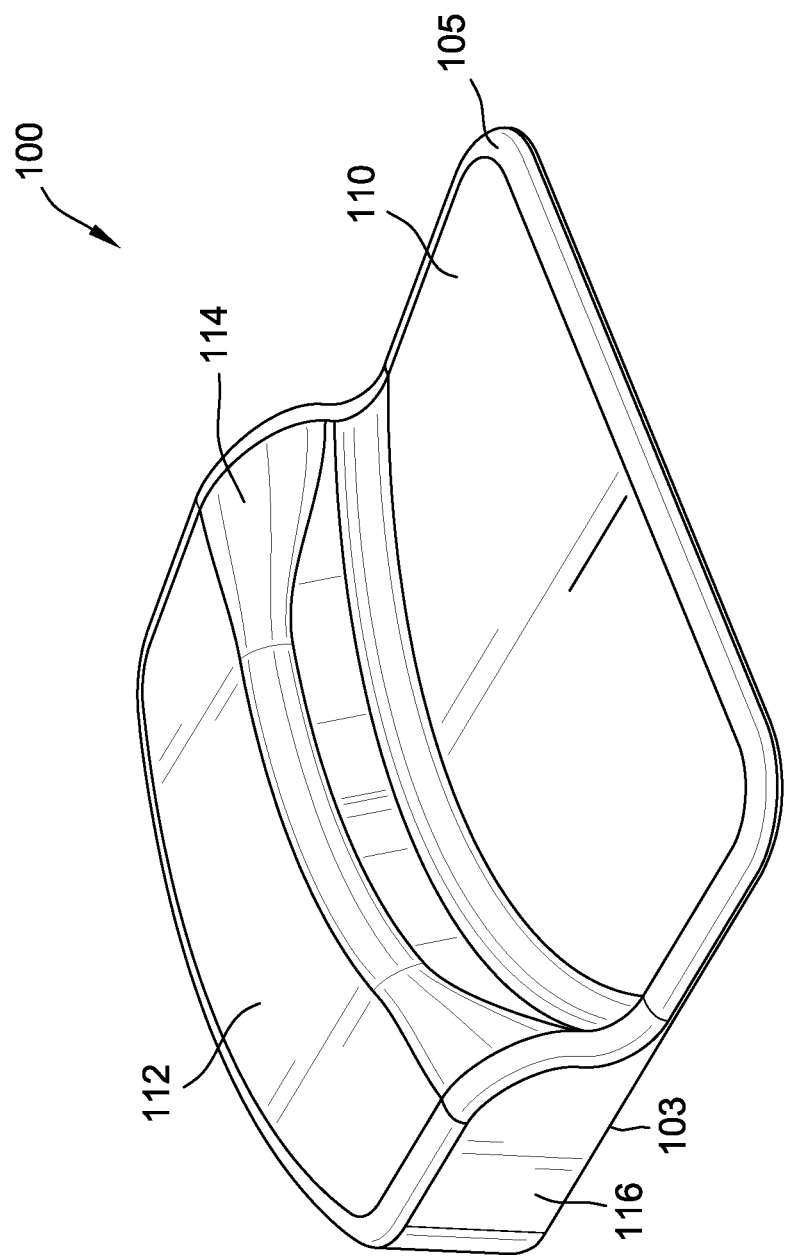
FIG. 1 is an isometric view of an exemplary embodiment of the present invention.

During use of a foot pedal and depression of the treadle, a user may experience heel rise as force is exerted on the toes and/or the ped of the foot or have to move the foot forward on the treadle to achieve adequate control and pressure to actuate the treadle resulting in the heel not being in a comfortable and relaxed position during operation of the foot pedal. In order to reduce or eliminate heel rise and/or provide adequate heel support while keeping the same configuration of the foot pedal and the associated treadle, a heel cup extender may be used to shift the user's heel location forward to reduce or eliminate heel rise and muscle fatigue of the leg and foot. As illustrated in FIG. 1, heel cup extender 100 may have a duckbill shape having an upper top portion 112 and a lower top portion 110 separated by heel wall 114. Edge 105, which may be rounded, may traverse the outer boundary of each of top portion 112, heel wall 114, and lower top portion 110. Lower top portion 110 may have a larger surface area than upper top portion 112 with each parallel to each other. Heel wall 114 may be concave or otherwise curved and may, for example, comprise a plurality of rounded portions, with such features designed to ergonomically accommodate a user's heel. Side wall 116 may wrap around the vertical perimeter of the heel cup extender 100. For example, side wall 116 may be situated between edge 105 and bottom portion 103.

Figure 1A:
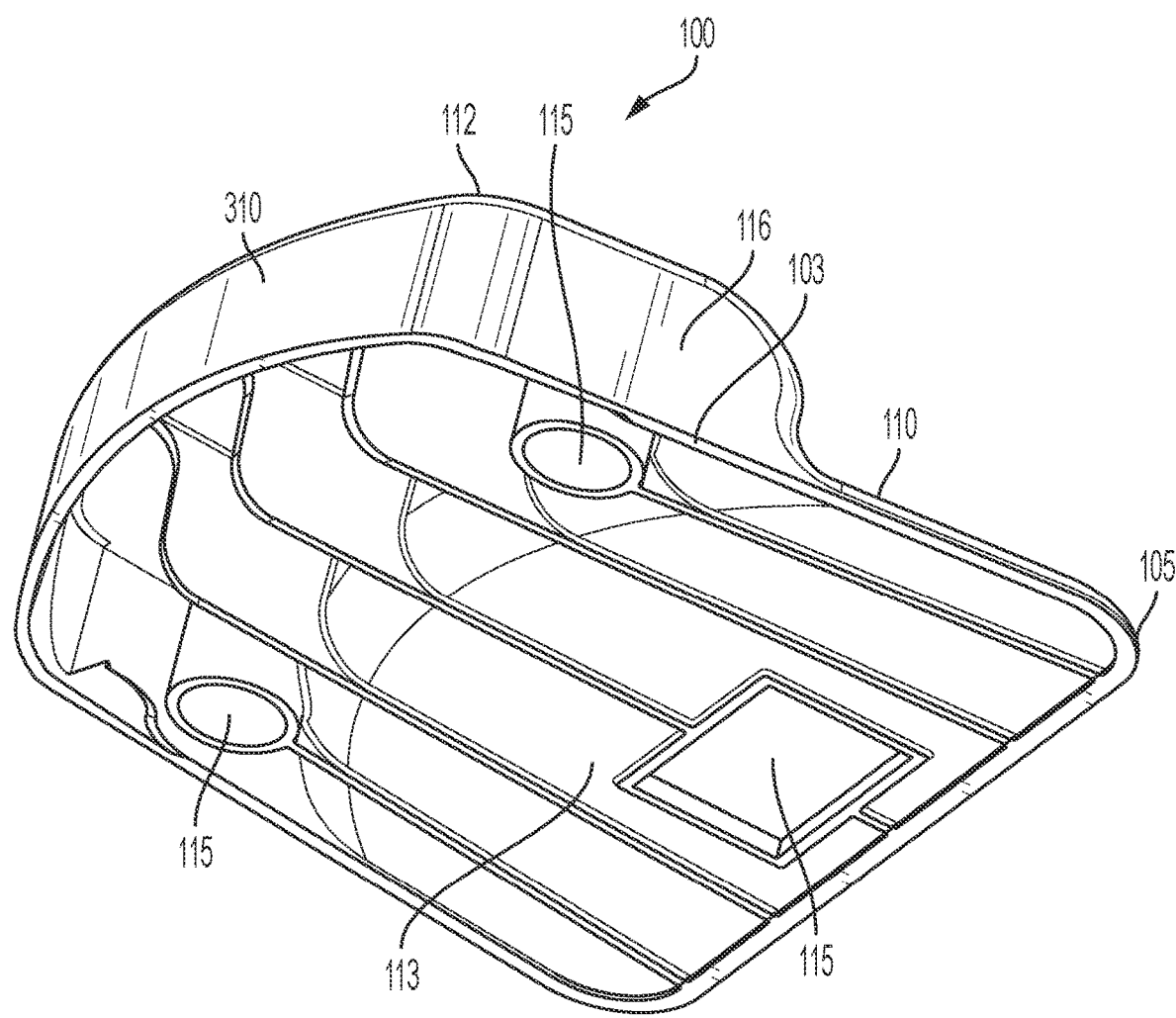
FIG. 1A is an isometric view of an exemplary embodiment of the present invention.
Figure 5:
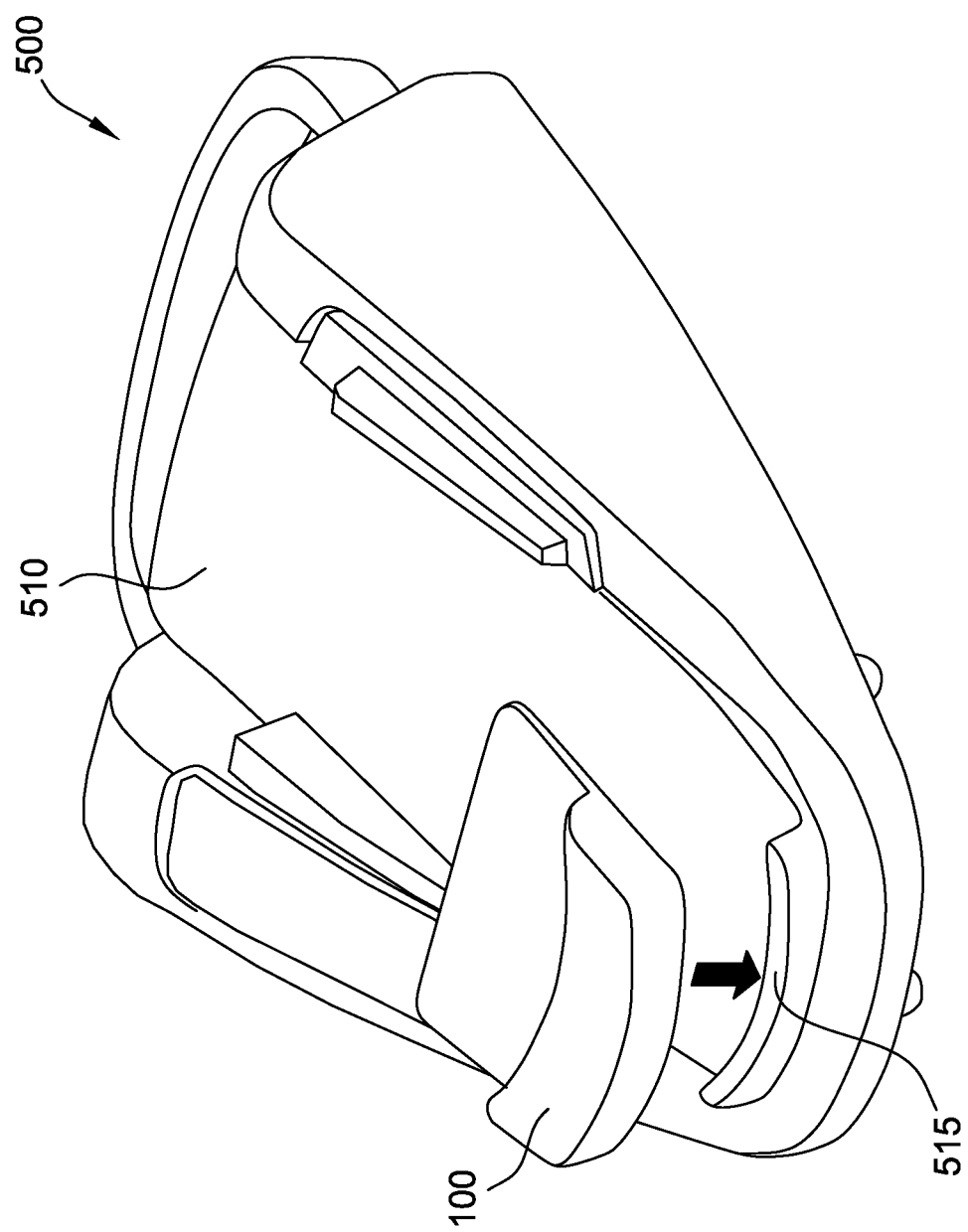
FIG. 5 is an illustration of an exemplary embodiment of the present invention.

As illustrated in FIG. 1A, heel cup extender 100 has a bottom side 113 configured to couple with a surface of treadle 510 of foot pedal 500 (shown in FIG. 5). Bottom side 113 may include one or more magnets 115 for coupling the heel cup extender 100 with the treadle 510 by a magnetic force. In an example, there may be one or more magnets 115 located towards the distal end of the heal cup extender 100 and/or one or more magnets 115 located towards the proximal end of the heel cup insert 100.

Figure 2:
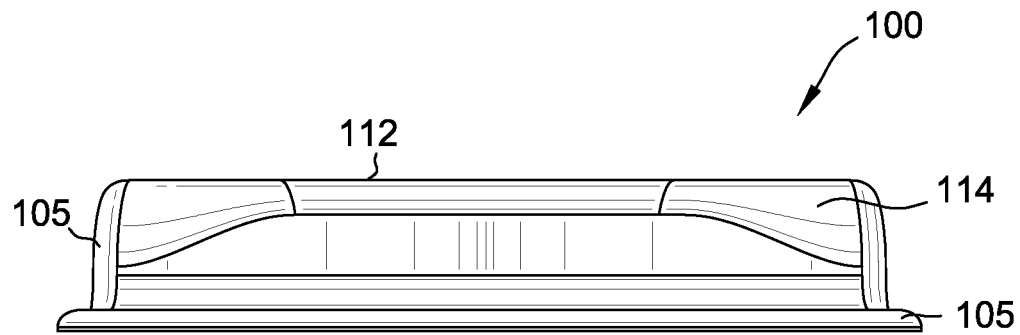
FIG. 2 is a front view of an exemplary embodiment of the present invention.
Figure 3:
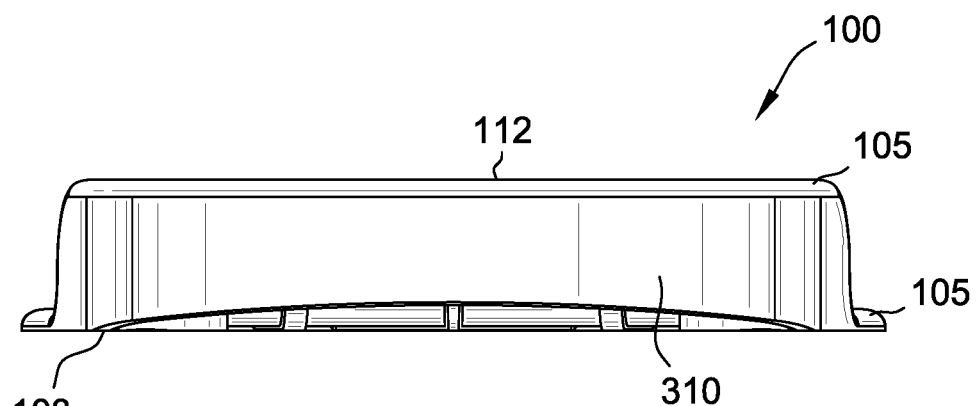
FIG. 3 is a rear view of an exemplary embodiment of the present invention.
Figure 4:
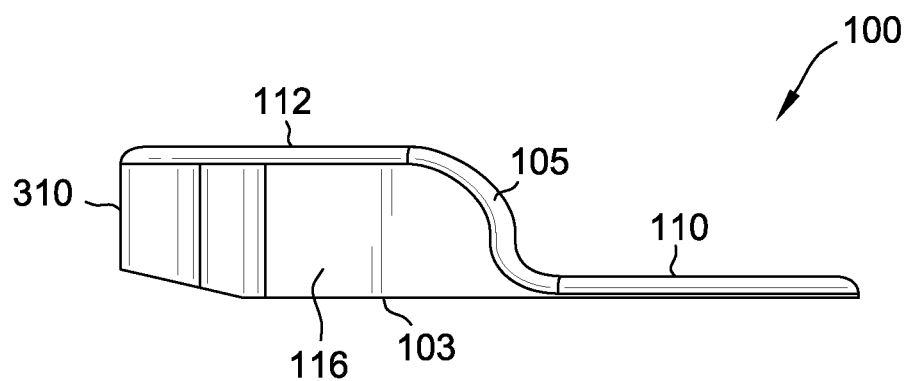
FIG. 4 is a side view of an exemplary embodiment of the present invention.

Various views of heel cup extender 100 are shown in FIGS. 2-4. For example, a front view of heel cup extender 100 is illustrated in FIG. 2 and may more clearly illustrate rounding on heel wall 114 along the intersection with upper top portion 112 which may allow a user's heel to more easily seat onto lower top portion 110 if the user's heel comes into contact with upper top portion 112 before lower portion 110, for example. The concave shape of heel wall 114 may also provide the user with a tactile indication as to the near center of the heel wall 114 of the heel cup extender 100. Upper top portion 112 may also provide a larger area in which a user may rest their heel during use of the foot pedal while the lower top portion 110 may have a length sufficient to reach to our beyond the arch of the user's foot to minimize any interference between the insert and the foot pedal treadle on which the heel insert may rest.

FIG. 3 illustrates a back view of heel cup extender 100 and illustrates the rear portion 310 of side wall 116. In an embodiment, rear portion 310 may be shorter than the remainder of side wall 116 and may include an angular and/or concave shape distal from upper top portion 112 and may be bounded by edge 105 at the top and by bottom portion 103 at the bottom. An angular shape of the rise which may be associated with rear portion 310 is further illustrated in FIG. 4. Rear portion 310 of sidewall 116 may be rounded and shaped to fit against the heel cup portion of an existing foot pedal assembly. The union of rear portion 310 of sidewall 116 to bottom portion 103 may be angular and may form greater than a right angle.

In an embodiment of the present invention, the heel cup insert may further comprise at least one magnetic portion to facilitate simple installation and removal of the heel cup insert into an existing foot pedal. The use of a magnet portion may allow for the attachment and removal of the heel cup insert without the use of tools while also making installation and removal intuitive to a user. The magnetic portion may comprise one or more removal magnets inserted into the bottom of the heel cup insert. The magnetic force between the heel cup insert and the foot pedal should be sufficiently strong enough to allow the heel cup insert to remain firmly in place during use with the foot pedal while also not attracting other proximately located metallic objects. Similarly, the magnetic force should prevent inadvertent disconnection of the heel cup inset while carrying the foot pedal from the heel end with the heel cup insert in place.

As illustrated in FIG. 5, heel cup extender 100 may be placed at the proximal end of treadle 510 of foot pedal 500. The heel cup extender 100 may mate on top of the treadle's heel stop 515 by, for example, magnetic attachment. One or more magnets may be placed at any location on the base of the heel extender to enable mating with treadle 510. In an embodiment of the present invention, one or more additional magnets may be located under the lower top portion 110 to more strongly attach the heel cup extender 100 to the treadle 510. In another embodiment, the location of a majority of the magnets may be placed away from the proximal end of the treadle to minimize the likelihood that other metal objects will be attracted to the foot pedal due to the magnets of the heel insert, such as, for example, a surgical tool which may have fallen to the floor. In an embodiment of the present invention, the the magnets may be placed away from the distal end of the heel insert which may increase the total moment arm needed to remove the heel insert from the foot pedal. This increase in attachment strength of the heel cup insert to the foot pedal treadle may allow the heel cup insert to be utilized as a handle by the user for transporting the foot pedal between various locations.

Although the strength of the magnets used may vary by desired application, in an embodiment of the present invention, the magnets were strong enough to allow a user to place their fingers on the edge of the heel insert and to lift the whole of the foot pedal just from the heel insert without the heel insert dislodging. As would be appreciated by those skilled in the art, the necessary strength of the magnetics will be proportional to the amount of ferromagnetic or near-ferromagnetic material in the treadle of the foot pedal. Similarly, the composition and thickness of any covering on the treadle of the foot pedal may need to be considered when configuring the amount of magnetism desired for the heel insert.

The use of the heel cup insert may improve the ergonomic fit of a user's foot to a particular foot pedal and may increase the usability and reliability for a given user. Similarity, the heel cup insert may reduce discomfort and fatigue associated with using a foot pedal without the heel cup insert, especially when used for a long period of time. The heel cup insert may also reduce the difficulty some user's may have reaching and activating switches on the distal end of the foot pedal, especially for small-footed users.

As would be appreciated by those skilled in the art, the heel cup insert may be seated onto the foot pedal treadle with another attachment means. For example, an adhesive may be used and may allow the heel insert to be permanently affixed or may allow it to be removably affixed. For example, a tacky substance may be used which may prevent the heel insert from moving during use, but remain removable between users. Alternatively, instead of magnetic attachment, the heel cup insert may be attached to the treadle by a mechanical fit through such means as an interference fit, fasteners, a snap fit, and/or other mechanical combination.

The heel insert may also be available in various sizes to accommodate both differences in treadle design and various size heels and feet. The heel cup insert may be designed for limited use, such as for single use, and may, for example, comprise pliable materials to increase the comfort of the user and the accommodation of the users' heel in the heel cup insert.

Figure 6:
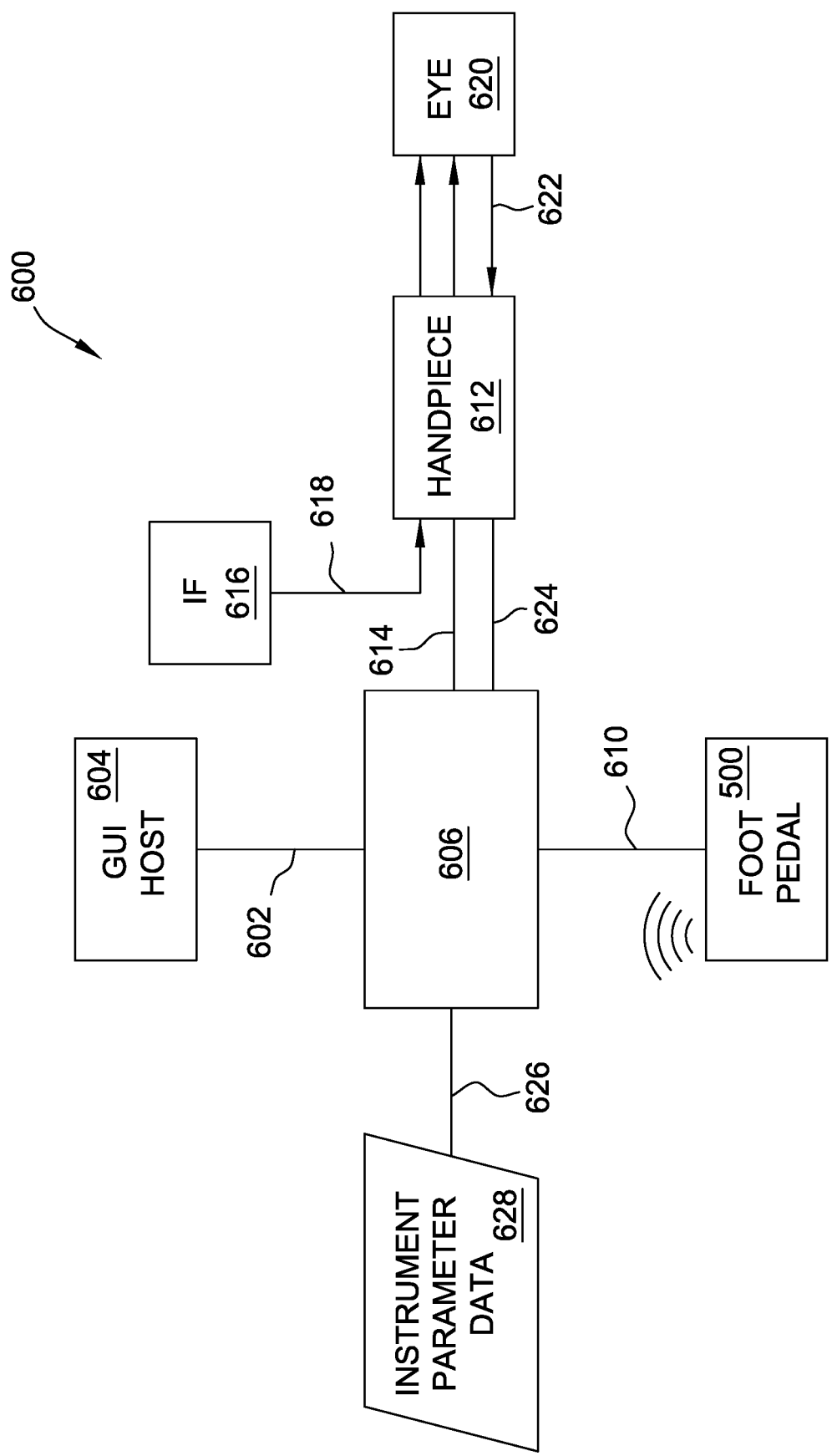
FIG. 6 is a schematic illustration of an exemplary embodiment of the present invention.

Although the present foot pedal control may be used in various environments and applications, a particularly useful application is in an ocular surgical system such as a pha-coemulsification/vitrectomy system. An exemplary pha-coemulsification/vitrectomy console system 600 for use in such an application is illustrated in the functional block diagram of FIG. 6. More particularly, FIG. 6 shows selected ones of the components and interfaces that may be employed in a safety-critical medical instrument system in which the foot pedal controller disclosed herein may be utilized.

A serial communication cable 602 may connect a GUI 604 and console 606 for the purposes of controlling the console 606 by the GUI host 604. The console 606 may be considered a computational device in the arrangement shown, but other arrangements are possible. A switch module associated with an exemplary foot pedal 500, such as described herein, transmits control signals relating internal physical and virtual switch position information as input to the console 606 over a serial communications cable 610, or wirelessly if desired. Console 606 may provide a database file system for storing configuration parameter values, programs, and other data saved in a storage device (not shown). In addition, the database file system may be realized on the GUI host 604, console 606, or any other subsystem (not shown) that could accommodate such a file system.

The system 600 has a handpiece 612 that typically includes a needle and electrical means, such as a piezoelectric crystal, for ultrasonically vibrating the needle. The console 606 supplies power on line 614 to handpiece 612. An irrigation fluid source 616 can be fluidly coupled to handpiece 612 through line 618. The irrigation fluid and ultrasonic power are applied by handpiece 612 to an eye 620, or other affected area or region. Alternatively, the irrigation source may be routed to the eye 620 through a separate pathway independent of the handpiece. Aspiration is provided from the eye 620 by one or more pumps (not shown), such as a peristaltic pump and/or venturi pump, via the console 606, through lines 622 and 624. A surgeon/operator may select an amplitude of electrical pulses either using the handpiece, via the instrument host and GUI host, using the foot pedal, and/or voice command.

In an embodiment, an interface communications cable 626 connects to the console 606 for distributing instrument sensor/parameter data 628, and may include distribution of instrument settings and parameter information, to other systems, subsystems and modules within and external to console 606. Although shown connected to the console 606, interface communications cable 626 may be connected or realized on any other subsystem (not shown) that could accommodate such an interface device able to distribute the respective data.

Those of skill in the art will appreciate that the herein described apparatuses, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather are to be accorded the widest scope consistent with the principles and novel features disclosed herein.

What is claimed is:

1. A heel shifting device, comprising:
 a heel cup insert configured to fit near the proximal end of a foot pedal suitable for receiving the heel of a user, wherein the heel cup insert is attached to the foot pedal by a magnetic force.

2. The device of claim 1, wherein the heel cup insert comprises a first top portion between the foot pedal and the heel of the user.

3. The device of claim 1, wherein the heel cup insert comprises a second top portion on which the heel of the user rests.

4. The device of claim 1, wherein the heel cup insert comprises at least one vertical wall portion for receiving the heel of the user.

5. The device of claim 1, wherein a plurality of magnets provides the magnetic force.

6. The device of claim 1, wherein a plurality of magnets located towards the distal end of the heel cup insert provides the magnetic force.

7. The device of claim 1, wherein a plurality of magnets located towards the proximate end of the heel cup insert provides the magnetic force.

8. The device of claim 1, wherein the heel cup insert provides the magnetic force.

9. The device of claim 1, wherein the heel cup insert is used as a handle to carry the foot pedal.

10. A surgical system for phacoemulsification, comprising:
 a foot pedal communicatively associated with a surgical console, wherein the foot pedal comprises:
  a treadle portion on the foot pedal for receiving a user's foot, wherein the treadle portion comprises a proximal end and a distal end; and
  a heel stop located at the proximal end of the treadle portion and configured to support a heel of the user's foot; and
 a heel cup insert removably attached to the treadle portion and configured to shift the user's foot toward the distal end, wherein the heel cup insert is removably attached to the treadle portion by a magnetic force.

11. The surgical system of claim 10, wherein the heel cup insert comprises a raised portion between the treadle portion and the back of the heel of the user.

12. The surgical system of claim 10, wherein the heel cup insert comprises a flat top portion on which the bottom of the user's heel rests.

13. The surgical system of claim 10, wherein the heel cup insert comprises at least one curved vertical wall portion for ergonomically receiving the heel of the user.

14. The surgical system of claim 10, wherein a plurality of magnets provide the magnetic force.

15. The surgical system of claim 10, wherein a plurality of magnets located towards the distal end of the heel cup insert provides the magnetic force.

16. The surgical system of claim 10, wherein a plurality of magnets located towards the proximal end of the heel cup insert provides the magnetic force.

17. The surgical system of claim 10, wherein the heel cup insert provides the magnetic force.

18. The surgical system of claim 10, wherein the heel cup insert is used as a handle to carry the foot pedal.

* * * * *